United States Patent [19]

Lee et al.

[11] 4,197,418
[45] Apr. 8, 1980

[54] HEAT DISPOSED IN LOWER ALCOHOLS AND DERIVATIVES CONVERSION TO GASOLINE HYDROCARBONS IN A CRYSTALINE ZEOLITE FLUIDIZED BED

[75] Inventors: Wooyoung Lee, Cherry Hill, N.J.; Sergei Yurchak, Media, Pa.

[73] Assignee: Mobil Oil Corporation, New York, N.Y.

[21] Appl. No.: 16,596

[22] Filed: Mar. 1, 1979

[51] Int. Cl.² .................... C07C 11/00; C07C 15/02
[52] U.S. Cl. .................... 585/469; 208/120; 585/302; 585/408; 260/449.6 R
[58] Field of Search ............ 208/120; 585/408, 302, 585/469; 260/449.6

[56] References Cited

U.S. PATENT DOCUMENTS

| | | | |
|---|---|---|---|
| 2,373,008 | 4/1945 | Becker | 260/449.6 |
| 3,351,548 | 11/1967 | Payne et al. | 208/120 |
| 3,926,778 | 12/1975 | Owen et al. | 208/120 |
| 3,969,426 | 7/1976 | Oweu et al. | 585/302 |
| 3,998,899 | 12/1976 | Daviduk et al. | 585/469 |
| 4,013,732 | 3/1977 | Chang et al. | 585/408 |
| 4,035,430 | 7/1977 | Dwyer et al. | 585/408 |
| 4,044,061 | 8/1977 | Chang et al. | 585/408 |
| 4,046,825 | 9/1977 | Owen et al. | 585/408 |
| 4,052,479 | 10/1977 | Chang et al. | 585/469 |
| 4,071,573 | 1/1978 | Owen et al. | 585/469 |
| 4,118,337 | 10/1978 | Gross et al. | 208/120 |
| 4,118,338 | 10/1978 | Gross et al. | 208/120 |
| 4,118,431 | 10/1978 | Cheu | 585/906 |

Primary Examiner—Veronica O'Keefe
Attorney, Agent, or Firm—Charles A. Huggett; Carl D. Farnsworth

[57] ABSTRACT

A method and means for disposing of undesired heat in the conversion of lower alcohols and their derivatives to higher boiling gasoline hydrocarbons in a crystalline zeolite fluidized bed.

9 Claims, 2 Drawing Figures

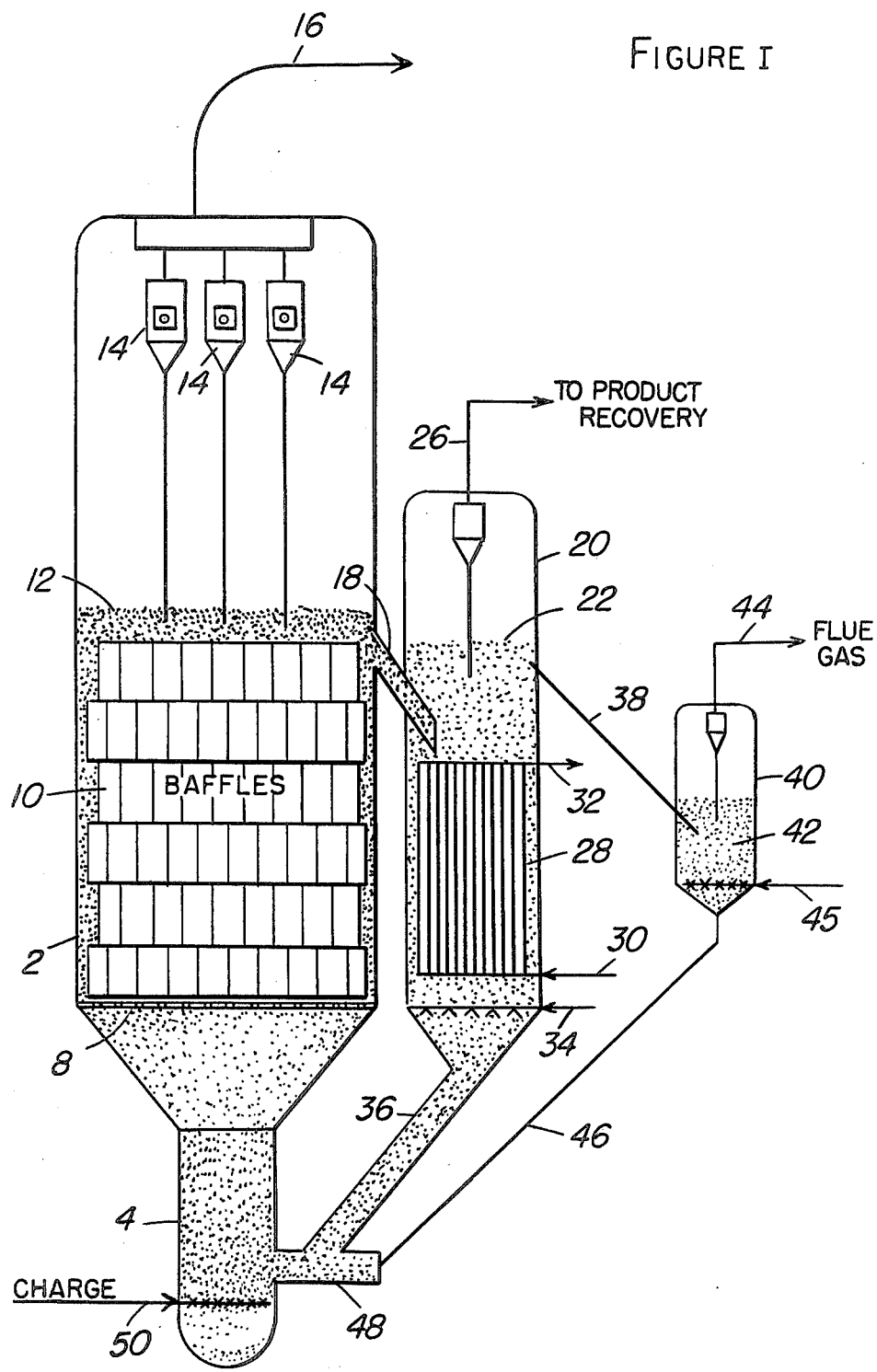
FIGURE I

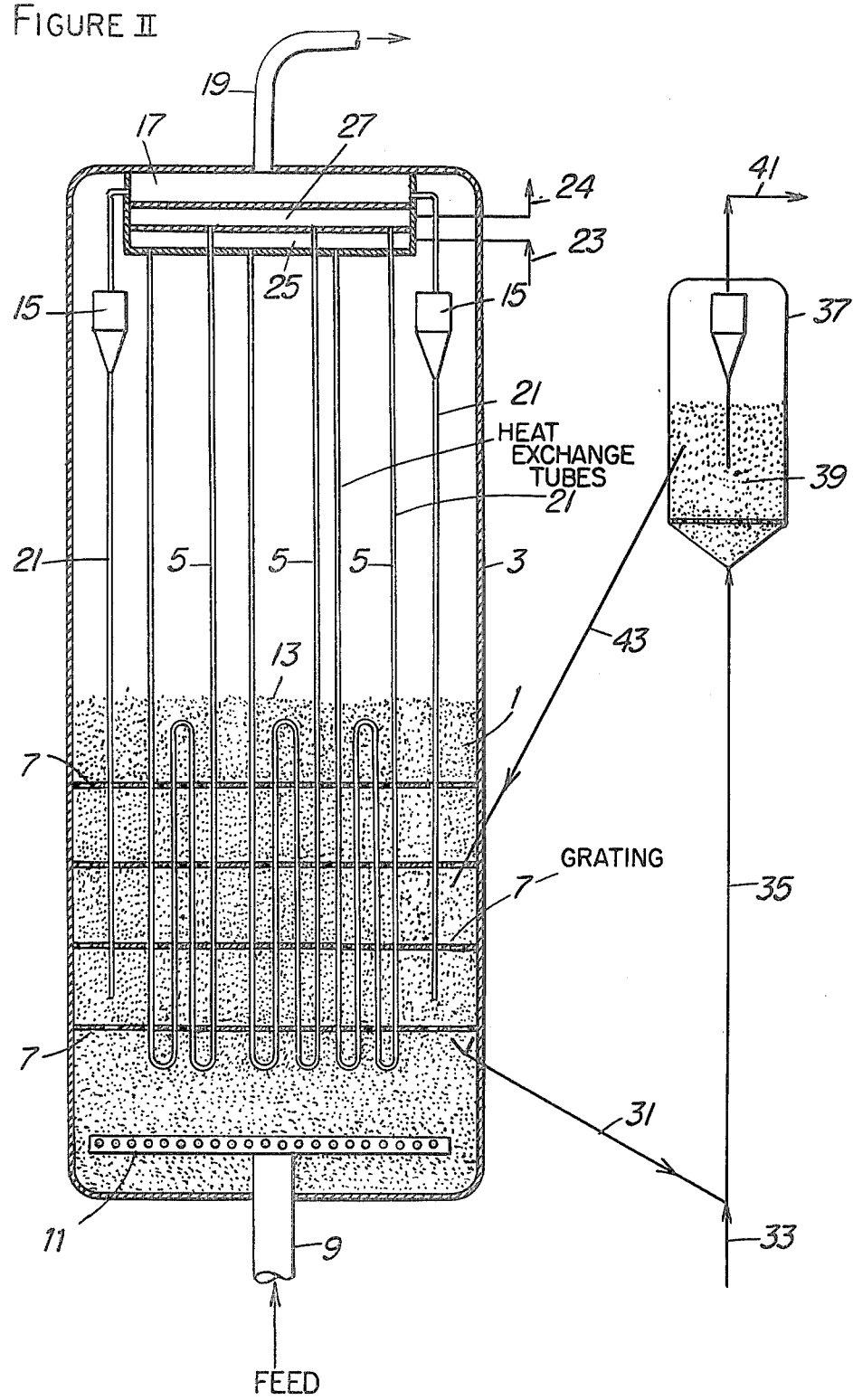
FIGURE II

HEAT DISPOSED IN LOWER ALCOHOLS AND DERIVATIVES CONVERSION TO GASOLINE HYDROCARBONS IN A CRYSTALINE ZEOLITE FLUIDIZED BED

BACKGROUND OF THE INVENTION

The application of fluidized catalyst techniques developed particularly in the petroleum industry for effecting chemical reaction embodying the distribution of heat and/or the disposal of undesired heat has long been accepted as a major processing tool of the industry. For example, the catalytic cracking of oil vapors to produce lower boiling desired products and regeneration of the catalyst used in such an operation has been particularly useful for fluidized catalyst techniques. It has also been proposed to use the fluidized catalyst technique in the highly exothermic reactions of Fischer-Tropsch synthesis and the known Oxo process primarily for the disposal of generated heat. In many of the fluidized catalyst operations developed, disposal of the reaction heat has been accomplished by many different techniques including transfer of catalyst through cooling sections and/or including indirect cooling means with a fluid bed of catalyst to absorb reaction heat transferred by the finely divided fluidized catalyst particles. Not only is the fluidized catalyst technique used for temperature control by addition and/or removal but it has also been found useful for extending the active life of the catalyst used in the process.

The present invention is concerned with an arrangement and method of operation for disposing of generated exothermic reaction heat within limits which will provide desired product selectivity and prolong the useful life of the catalyst employed in the chemical conversion operation. U.S. patents considered in the preparation of this application include U.S. Pat. Nos. 2,373,008; 3,480,408; 3,969,426; 4,013,732; 4,035,430; 4,044,061; 4,046,825; 4,052,479; 4,071,573 and 4,118,431.

SUMMARY OF THE INVENTION

This invention relates to the method amd means for effecting chemical reactions in the presence of a select class of particulate crystalline zeolites. More particularly, the present invention is concerned with effecting exothermic chemical reactions in the presence of crystalline zeolites of selected crystal arrangement particularly promoting the formualtion of hydrocarbon product materials higher boiling than the reactant charge material. In a more particular aspect, the present invention is concerned with effecting the conversion of lower alcohols and derivatives thereof in a fluidized mass of particulate material comprising a selected class of crystalline zeolite providing a pore dimension greater than about 5 Angstroms and pore windows of a size provided by 10-membered rings of oxygen atoms. In a more particular aspect, the present invention is concerned with the method and means for effecting the conversion of compounds of carbon and hydrogen with and without combined oxygen in a fluid bed of catalyst particles to higher boiling products in the gasoline boiling range.

The crystalline aluminosilicate zeolites utilized herein are members of a novel class of zeolites that exhibits unusual properties. Although these zeolites have unusually low alumina contents, i.e. high silica to alumina ratios, they are very active even when the silica to alumina ratio exceeds 30. The activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which, due to pore or to other cause, may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of normal hexane and 3-methylpentane over a small sample, approximately one gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Contraint Index of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-35 | 4.5 |
| ZSM-38 | 2 |
| TMA Offretite | 3.7 |
| Beta | 0.6 |
| ZSM-4 | 0.5 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-35, and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.57 |
| Levynite | .40 | 1.54 |
| Erionite | .35 | 1.51 |
| Gmelinite | .44 | 1.46 |
| CHabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5% by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, silica-titania as well as ternary compostions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely, with the zeolite content ranging from between about 1 to about 99% by weight and more usually in the range of about 5 to about 80% by weight of the dry composite.

The present invention is concerned with a method as applied to two different systems for effecting the exothermic conversion of hetero type compounds, ethers and carbonyl compounds with a fluid mass of catalyst particles in a manner particularly promoting the formation of olefinic and/or aromatic compounds. More particularly, the present invention is concerned with a method and systems employed for dispersing the exothermic heat of chemical reaction generated in the preparation of olefinic and/or aromatic and related compounds by contacting a fluidized catalyst comprising ZSM-5 crystalline zeolite with one or more reactants selected from the group consisting of alcohols, ethers, carbonyl compounds, and mixtures thereof.

Referring now to FIG. 1 by way of example, there is shown a substantially vertical and elongated reactor vessel 2 provided with a lower reactant-catalyst mixing section 4 through which a mixture of reactants and a fluidizable mass of catalyst particles pass upwardly under restricted exothermic reaction conversion conditions as herein provided. The mixture of catalyst particles and reactants is initially formed in a relatively short riser section generally represented by conduit 4 feeding into the bottom of a larger-diameter reaction vessel. The suspension is initially formed under conditions to provide a mix temperature in the range of about 400° F. to about 600° F. which is thereafter passed through the lower bottom conical portion 6 of the reactor vessel and distributor grid 8 for flow upwardly therethrough into vessel portion 2 wherein a more dense phase of upflowing catalyst in reactant material is maintained. Vessel 2 is provided with vertically positioned gas bubble breaking means to provide a plurality of means 10 or other suitable open space baffle means alternately staggered in the vertical height of the catalyst bed. Thus the space above grid 8 up to about the catalyst bed level 12 is filled with baffle means placed across the vessel 2 at spaced apart intervals for the purpose of dispersing or breaking up any formed gas or reactant bubbles to be less than 6 inches in diameter and preferably not more than 4 inches in diameter in the generally upflowing catalyst-reactant suspension passing upwardly through the vessel. The horizontally disposed but vertically misaligned baffles may be half pipe sections, angular baffles, or honeycomb sections vertically displaced with respect to horizontal sections and sized to provide the bubble restrictions herein defined. On the other hand, the catalyst bed between grid 8 and surface 12 may be provided with heat exchange means comprising tubular heat exchange means or bayonet type heat exchange tubes arranged to restrict gas bubble formation as herein defined. Whatever arrangement is utilized to limit bubble growth, it is important that the reactant and product thereof be essentially plug flow upwardly through the mass of catalyst above grid 8 and that the catalyst mass be randomly mixed to minimize temperature gradient in the fluid bed or mass of catalyst. Thus it is desirable to maintain isothermal temperature conditions within the generally upflowing random mixed catalyst mass. The dispersal of generated exothermic heat is influenced by one of the gas bubble dispersing or mixing means and/or heat exchange means provided in the upflowing fluid catalyst within the reactor vessel. In the particular arrangement of FIG. 1, it is preferred that the mixture of recycle catalyst and regenerated catalyst be at a temperature of about 600° F., so that, upon contact with vaporous methanol charge, the temperature rise in the catalyst system will be restricted so that the catalyst bed temperature at its upper level 12 will not be above about 765° F. In this operating arrangement, it is desirable to employ gas velocities and a contact time which will restrict the temperature rise in the catalyst bed above grid 8 not to exceed about 110 degrees. On the other hand, a contact time between catalyst and reactant of at least 20 seconds is desirable. More particularly, it is preferred that a reactant-catalyst contact time of at least 23 or 25 seconds be provided in the system of FIG. 1.

In the conversion of methanol and related hetero compounds contemplated by this invention, the exothermic temperature buildup will be greater than that contributed by the conversion of ethers and carbonyl compounds. On the other hand, if carbon monoxide and/or hydrogen is combined with any one of these reactant feeds, there will be a proportional increase in exothermic heat as a function of these materials reacting with one another and/or the other feeds comprising alcohols, ethers and carbonyl compounds. In any event, it is preferred to maintain a very close temperature control on the various reactions promoted by the ZSM-5 type crystalline zeolite; it being desirable to restrict the conversion of methanol to aromatics to a temperature within the range of 500° F. to 900° F.; the conversion of ethers to aromatics to a temperature within the range of 500° F. to 900° F.; and the conversion of the carbonyl type feed to a temperature within the range of 500° F. to 900° F. More particularly, however, it is preferred that the temperature be restricted not to exceed 800° F. The operating pressure for these various reactions may be confined within the range of atmospheric to 200 psig, more usually up to about 100 psig and preferably not above 50 psig. The reactant space velocity is preferably selected from within the range of 0.5 to 5 v/v/hr. and more usually not above 3 v/v/hr. to provide a reactant residence time in contact with the catalyst within the limits of 15 to 30 seconds and more usually at least about 20 or 23 seconds.

In the arrangement of FIG. 1, the reactant feed comprising methanol with or without water in vapor or liquid form alone or mixed vapor and liquid methanol is charged to mixing zone 4 for admixture with finely divided fluidizable catalyst particles comprising ZSM-5 crystalline material charged to conduit 4 beneath the bottom conical portion of reactor vessel 2. Conduit 4 provides a limited mixing and reaction time, and some temperature rise to occur before passing through grid 8 and into a larger-diameter upflowing catalyst suspension reaction zone baffled or provided with heat exchange means restricted as herein provided.

In the upper portion of vessel 2 above catalyst bed level 12, a more dispersed catalyst phase exists which is separated by cyclones 14. When the dispersed phase is in an expanded section of the reactor, the upflowing suspension encounters a reduction in velocity which causes a separation of catalyst particles from entraining reaction vapors. The vapors pass through cyclonic separation means represented by separators 14 provided with suitable catalyst diplegs for returning cyclonically separated catalyst to the more dense mass of catalyst therebelow. Vaporous material denuded of catalyst particles by cyclonic separation is removed from the upper portion of the vessel by conduit 16 communicating with product recovery and separation equipment not shown.

The mass of catalyst particles passing upwardly through reactor section 2 and forming an upper phase level 12 acquires an elevated exothermic reaction temperature as herein provided and requires cooling of a major portion thereof before return to mixing zone 4. Thus, the catalyst is withdrawn from beneath upper catalyst bed level 12 by conduit 18 and is passed to a separate catalyst stripping and cooling zone 20 adjacent reaction zone 2. In stripping zone 20, the catalyst is passed downwardly therethrough countercurrent to rising stripping and fluidizing gas. Steam, light product gases or other gases suitable for use in the process and easily separated from the reaction product may be used for this purpose. The catalyst charged to stripper 20 acquires an upper bed level 22. Cyclonic separating means 24 are provided for removing catalyst particles from stripped product. The gaseous product of stripping is removed by conduit 26.

In the lower portion of stripping zone 20, there is provided a heat exchange means 28 provided with coolant inlet means 30 and outlet means 32. In one arrangement, specifically shown in the figure, boiler feed water, for example, is introduced by conduit 30 for producing steam at an elevated pressure of about 600 psig and removed therefrom by conduit 32. The stripping gas is introduced to a bottom portion of the stripper by conduit 34 and beneath heat exchanger 28. In this stripping and cooling operation, the catalyst is cooled from a temperature usually above 750° F. to a temperature of about 600° F. or within the range of 550° F. to 650° F. The stripped and cooled catalyst is withdrawn from the bottom of stripper 20 by conduit 36 communicating with reactant-catalyst mixing zone 4 for use as herein provided.

In another embodiment, it is comtemplated employing heat exchanger 28 to preheat the reactant feed sufficient to vaporize the feed. That is, liquid methanol may be charged by conduit 30 to the heat exchanger 28, withdrawn by conduit 32 in vaporous condition and thereafter passed by conduit means not shown to a bottom portion of mixing zone 4. On the other hand, the vaporous methanol thus obtained may be used in conjunction with some liquid methanol feed to obtain a desired mix temperature with catalyst charged thereto. When charging vaporous methanol to the mixing zone, it is contemplated forming a mix temperature of about 565° F. with the charged catalyst. In the combination above described, it is also comtemplated dispensing with heat exchanger 28 and replacing the exchanger with suitable stripper baffle means to provide a tortuous flow path for catalyst and stripping gas to traverse within the stripper. In this arrangement, the stripping gas may be relied upon to effect some cooling of the stripped catalyst so that upon return to mixing zone 4 it may be relied upon to provide the necessary heat of vaporization of charged liquid methanol in the presence or absence of charged vaporous methanol.

In the arrangements above briefly discussed, the stripped product may be combined with the product recovered by conduit 16 from the reactor, or the stripped product may go to a preliminary separation step to recover hydrocarbons before combining the recovered hydrocarbons with the product withdrawn by conduit 16. It is important in the operations of the above arrangements to maintain two operating specifications during the fluid catalyst conversion of methanol to gasoline. That is, the reaction heat of 650 to 750 BTU per pound of methanol converted must be removed to maintain the reaction zone within design temperature limits and the conversion of methanol to hydrocarbons must be substantially complete, greater than 95% and more preferably greater than 99% complete. It is particularly desired for economic reasons to achieve on a once-through basis a methanol conversion to hydrocarbons of at least 99.5% in the fluid catalyst systems herein defined.

In the environment of exothermic chemical reactions contemplated by this invention, the catalyst particles are subject to some coke deactivation relatively slowly and some steam deactivation. Thus provision is made for removing coke deposits from only a portion of the circulated catalyst either continuously or intermittently. In this operation, it is not necessary therefore to remove all coke deposits during regeneration of the catalyst but only a portion of the deposited coke need be removed by burning in the presence of a combustion supporting gas such as air or an oxygen-enriched regeneration gas. It will be recognized by those skilled in the art that the activity of the catalyst can be restricted and controlled by level of residual coke retained on the catalyst. Such a control is highly desirable in the exothermic chemical conversion environment of this invention. That is, catalyst particles of restricted activity can be used with advantage in exothermic reactions of this invention.

To accomplish regeneration of the catalyst, a fluid catalyst regeneration operation is provided to which a small stream of catalyst of desired quantity may be passed for regeneration as herein provided. In the arrangement of FIG. 1, a stream of catalyst is withdrawn from an upper portion of the catalyst bed in stripper 20 by conduit means 38 for transfer to regenerator 40 containing a fluid bed of catalyst 42. Regeneration gas such as air is charged to a bottom portion of bed 42 by conduit 45 for flow upwardly therethrough under coke burning conditions. Regeneration of the catalyst may be accomplished at a temperature of about 900°0 F. or higher, it being preferred to keep the regenerator temperature as low as possible for achieving some limited and desired coke removal. Regeneration flue gas is recovered by conduit 44 and the regenerated catalyst is withdrawn by conduit 46. The regenerated catalyst in conduit 46 may be cooled in an indirect heat exchange means not shown before passing to a catalyst mixing zone 48 for admixture with recycled catalyst in conduit 36 recovered from the stripping zone. It will be recognized by those skilled in the art that several variations on the catalyst regeneration operation or technique may be employed. That is, a riser regeneration operation similar to that described by Payne et al. in U.S. Pat. No. 3,351,548 may be employed, or a combination of dense fluid bed catalyst regeneration and riser regeneration similar to that disclosed in U.S. Pat. Nos. 3,926,778 and 4,118,338 may be employed. Furthermore, the portion of catalyst to be regenerated may be withdrawn from a lower portion of the stripping zone than shown in FIG. 1, such as beneath the heat exchanger 28, and the regenerated catalyst may be added to an upper portion of withdrawal conduit 36 rather than a bottom portion thereof as shown in the drawing. As mentioned above, the regenerated catalyst in conduit 46 may pass through a heat exchange zone wherein water, steam or reactant material may be initially preheated before use as required or passage to heat exchange 28 or riser mixer 4. In the arrangement of FIG. 1, a reactant charge, such as methanol, ethers or mixtures thereof, is shown being introduced to the bottom portion of mixing zone 4 by conduit 50. The reactant charge may be liquid, vapor or charged as a mixture as above discussed. However, it is important that the exothermic temperature rise in riser mixing zone 4 be controlled to a low order of magnitude by mixing relatively cool catalyst, about 600° F. catalyst, with the reactant so that the upflowing catalyst-reactant mixture formed and passed through the reaction zone will not exceed an upper bed temperature limit restricted to not more than 900° F. and preferably not more than about 800° F.

FIG. 2 is a variation on the arrangement of FIG. 1 to the extent that a relatively dense randomly mixed fluid bed of catalyst 1 is maintained in a reaction zone 3 and temperature constraints in the fluid catalyst bed are maintained by any one of a combination of cooling coils 5. In addition, the fluid bed may be provided with horizontal baffles or grid means 7, there being a plurality thereof vertically spaced one above the other and restricted with respect to openings therein which will substantially minimize gas bubble growth in the catalyst bed not to exceed desired limits. That is, it is desired to limit gas bubble growth passing upwardly through the bed to less than 6 inches in diameter and preferably not more than 4 inches in diameter. Thus the distance between vertically extending heat exchange pipes, horizontal grid means and combinations thereof will vary with the size of grid opening and/or velocity of reactant passing upwardly through the catalyst mass, heat exchange surfaces and grids positioned therein.

In the above general arrangement, the reactant, such as methanol, is charged to reactor 3 by conduit 9 communicating with horizontal reactant distributor means 11. The feed may be charged in the vapor or liquid form. The methanol reactant upon contact with the catalyst will rapidly rise in temperature because of the reaction exotherm, but will be restricted by operating conditions to be less than the total temperature rise permitted in the reaction system. In this arrangement, the reactant passes upwardly through the fluid mass of catalyst under temperature restricted conditions to be less than 800° F. and contact time between reactant and catalyst to be at least 20 seconds and sufficiently high to achieve at least 99.5% conversion of methanol in the charged feed.

The products of reaction separated from the upper surface 13 of catalyst bed 1 pass through cyclone separating means 15 for removal of catalyst fines before passing to plenum chamber 17 and removal therefrom by conduit 19. Catalyst particles separated in cyclones 15 are returned to the bed of catalyst by diplegs 21.

In the arrangement of FIG. 2, the cooling coils hang from the top of the reactor vessel. That is, coolant is shown entering by conduit 23 to a distributor chamber 25 communicating with hanging heat exchange coils 5. The coolant after passing through the coils enters collecting chamber 27 before withdrawal by conduit 29. Other cooling coil arrangements may be employed in the reactor of FIG. 2 which will provide the cooling desired as well as gas bubble restrictions particularly desired. It is contemplated therefore using a vertically or horizontally positioned bundle of heat exchange tubes in the fluid catalyst bed with or without grid means 7, for example, to which coolant is added and withdrawn from reactor vessel 3. Other cooling arrangements known in the art may be used for this purpose without departing from the spirit of the invention.

Provision is made for removing catalyst from bed 1 for regeneration, and this may be accomplished by removing a relatively small stream of catalyst from a lower portion of the bed as shown by conduit 31, or it may be withdrawn from an upper portion of the bed and beneath bed interface 13. It is preferred that the withdrawn catalyst be stripped within a withdrawal well within the fluid bed of catalyst or in a suitable stripping vessel external to reactor 3. The withdrawn and stripped catalyst is then mixed with a regeneration gas such as air introduced by conduit 33 for passage through a riser regenerator 35 into regeneration zone or vessel 37. Additional regeneration gas such as a major portion thereof may be added directly to vessel 37 below grid 45 or by a pipe grid in place of or above grid 45. The suspension passed upwardly through riser 35 may terminate in the bottom portion of catalyst bed 39 if additional catalyst regeneration time is required or the riser may terminate above the bed of catalyst 39 within vessel 37. Flue gas products of combustion are removed from zone 37 by conduit 41 after passing through suitable cyclone separating equipment. The regenerated catalyst is passed from vessel 37 to reactor vessel 3 by conduit 43. The regenerated catalyst is returned to catalyst bed 1 in an area which will accept the hotter regenerated catalyst without unduly upsetting the temperature constraints to be maintained within fluid bed 1. Some cooling of this regenerated catalyst either directly or indirectly may be accomplished in conduit 43 by means not shown.

In any of the apparatus arrangements mentioned above with respect to FIG. 2, it is important that the fluid bed of catalyst be baffled with heat exchange means alone or in combination with grid means in such proximity to one another that the reactant gas bubble growth for the space velocity employed is restricted to less than a 6 inch diameter bubble and the temperature rise within the fluid catalyst system is restricted not to substantially exceed about 800° F. and preferably is below 800° F., but not below about 700° F. A bed temperature within the range of 750° F. to 775° F. is particularly desirable. It is preferred that the reactant contact time with the catalyst be greater than 15 seconds, but not so long as to produce significant amounts of product boiling outside the gasoline boiling range. That is, it is desirable to limit the production of material such as durene.

Having thus generally described the method and processing system of the invention and specifically described a processing scheme in support thereof, it is to be understood that no undue restrictions are to be imposed by reason thereof except as defined by the following claims:

We claim:

1. A method for effecting exothermic chemical reactions in the presence of a select class of crystalline zeolites represented by ZSM-5 crystalline zeolite promoting the formulation of hydrocarbon product materials higher boiling than the reactant charge material which comprises, passing a lower alcohol alone or in admixture with an ether derivative thereof in admixture with said special crystalline zeolite as suspension initially formed at a temperature in the range of about 400° to 600° F. upwardly through a relatively short riser mixing zone discharging into the bottom portion of a dense fluid bed of catalyst maintained in a larger-diameter reaction zone, said dense fluid bed of catalyst restricted vertically throughout its cross-section to restrict upflowing reactant bubble growth not to substantially exceed about 6 inches during contact with catalyst particles under substantially reactant plug flow conditions, recovering a reactant product comprising gasoline boiling hydrocarbons from said fluid bed of catalyst at a temperature below 900° F. separate from catalyst particles, and passing catalyst particles from an upper portion of said dense fluid bed of catalyst through a cooling zone and thence to a bottom portion of said riser mixing zone.

2. The method of claim 1 wherein a portion of the catalyst passed to the cooling zone is passed to a catalyst regeneration zone before passage of regenerated catalyst to the riser mixing zone.

3. The method of claim 1 wherein a cooling fluid is in indirect heat exchange with said fluid bed of catalyst.

4. The method of claim 1 wherein the catalyst passed to said cooling zone is indirectly cooled with a cooling fluid.

5. The method of claim 1 wherein the reactant space velocity through the reaction zone is restricted to within the range of 0.5 to 5 v/v/hr. to provide a reactant residence time within the range of 15 to 30 seconds.

6. The method of claim 1 wherein the reactant comprises methanol in the vapor form and a temperature rise in the dense fluid catalyst bed is restricted not to exceed about 100 degrees.

7. The method of claim 1 wherein the reactant product comprises a mixture of olefins and aromatics.

8. The method of claim 1 wherein the catalyst charged to the bottom of the riser mixer is not above about 600° F. and the temperature at the upper level of the dense fluid bed of catalyst is restricted not to exceed about 765° F.

9. The method of claim 1 wherein the catalyst comprises ZSM-5.

* * * * *